United States Patent [19]
Maeda et al.

[11] Patent Number: 5,856,418
[45] Date of Patent: Jan. 5, 1999

[54] WATER-SOLUBLE MONOMER, WATER-SOLUBLE POLYMER AND THEIR PRODUCTION PROCESS AND USE

[75] Inventors: Yoshihiro Maeda; Shigeru Yamaguchi, both of Himeji, Japan

[73] Assignee: Nippon Shokubai Co., Ltd., Japan

[21] Appl. No.: 831,565

[22] Filed: Apr. 9, 1997

[30]     Foreign Application Priority Data

Apr. 16, 1996 [JP] Japan .................................. 8-093920
Apr. 16, 1996 [JP] Japan .................................. 8-093921

[51] Int. Cl.$^6$ ......................... C08F 120/58; C08F 130/04
[52] U.S. Cl. ............................................ 526/304; 526/240
[58] Field of Search ................................. 526/304, 240

[56]         References Cited

U.S. PATENT DOCUMENTS

| | | |
|---|---|---|
| 4,157,418 | 6/1979 | Heilmann . |
| 4,172,934 | 10/1979 | Heilmann .............................. 526/304 |
| 4,320,173 | 3/1982 | Coran et al. . |
| 5,369,142 | 11/1994 | Culbertson et al. ................... 523/116 |

FOREIGN PATENT DOCUMENTS

| | | |
|---|---|---|
| 0 441 563 | 8/1991 | European Pat. Off. . |
| 40 29 297 | 3/1992 | Germany . |
| S56-61471 | 5/1981 | Japan . |
| 4-258696 | 9/1992 | Japan . |
| WO89/01930 | 3/1989 | WIPO . |

OTHER PUBLICATIONS

Subasinghe et al., Synthesis of Acyclic and Dehydroaspartic Acid Analogues of Ac–Asp–Glu–OH and Their Inhibition of Rat Brain N–Acetylated α–Linked Acidic Dipeptidase (NAALA Dipeptidase), J. Med. Chem., 1990, pp. 2734–2744, vol. 33, No. 10, American Chemical Society.

*Primary Examiner*—Jeffrey Smith
*Assistant Examiner*—Wu C. Cheng

[57]         ABSTRACT

A water-soluble monomer is shown by general formula (1) below. This monomer, for example, can be obtained by reacting asparagic acid and maleic anhydride in an aqueous basic solution under cooled conditions. A water-soluble polymer has a structural unit of general formula (2) below and a weight-average molecular weight of about 800 to about 8,000,000, and is, for example, produced by polymerizing a monomer including the water-soluble monomer of general formula (1). The water-soluble polymer has excellent chelating and dispersing actions and therefore can favorably be used for various purposes, such as, detergent compositions, inorganic-pigment dispersants, fiber-treating agents, water-treating agents, wood pulp-bleaching assistants.

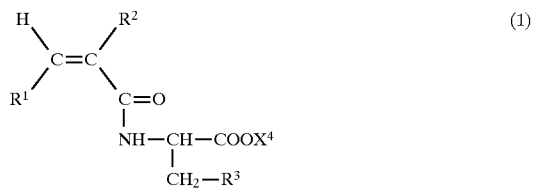

(1)

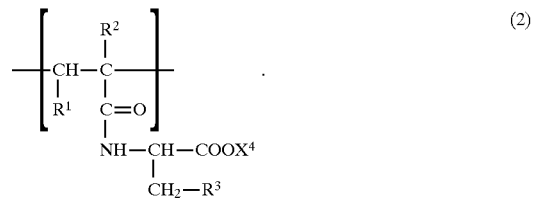

(2)

7 Claims, No Drawings

WATER-SOLUBLE MONOMER, WATER-SOLUBLE POLYMER AND THEIR PRODUCTION PROCESS AND USE

BACKGROUND OF THE INVENTION

A. Technical Field

The present invention relates to a water-soluble monomer, having a carbon-carbon unsaturated double bond and a carboxyl group, and a production process therefor, and also relates to a water-soluble polymer, a production process therefor, and a composition containing the polymer. This composition is, for example, a detergent composition, an inorganic-pigment dispersant, a fiber-treating agent, a water-treating agent, or a wood pulp-bleaching assistant.

B. Background Art

Hitherto, various organic chelating agents are, for example, used for detergent compositions, dispersants, flocculants, scale inhibitors, chelating reagents, fiber-treating agents, wood pulp-bleaching assistants, pH adjustors, and washing agents.

The organic chelating agents are exemplified by ethylenediaminetetraacetate; nitrilotriacetate; and carboxylic acid-based polymers, such as, homo- or co-polymers of maleic or acrylic acid. Ethylenediaminetetraacetate and nitrilotriacetate are known to have relatively high ability to effectively scavenge heavy-metal ions. In addition, the carboxylic acid-based polymers are known to display excellent chelating and dispersing actions upon inorganic particles, and therefore used over wide scope.

On the other hand, Japanese Unexamined Patent Publication (Kokai) No. S56-61471, U.S. Pat. Nos. 4,172,934 and 4,157,418 disclose monomers which are obtained by introducing one or more carboxyl groups into a carbon atom, which is a constituent of an unsaturated double bond, through an amide bond and an alkylene or phenylene group. Any of these monomers is an amide compound which is obtained by reacting acryloyl or methacryloyl chloride with an amino acid.

However, in terms of per unit weight, ethylenediaminetetraacetate and nitrilotriacetate cannot scavenge a large amount of metal and are also entirely insufficient in inorganic-particle dispersibility which is demanded in various utilization fields.

The aforementioned carboxylic acid-based polymers have structures in which carboxyl groups are directly bonded to carbon atoms of principal chains of the polymers. Therefore, free rotation of the carboxyl groups is hindered and the metal ion scavengeability is insufficient.

In addition, the preceding amide compound can form a polymer having a carboxyl group at a distant site from its principal chain. This polymer, however, has a problem in that its metal ion scavengeability is low, because the density of the carboxylic acid which is present near the principal chain of the polymer (the density of the carboxyl group which is bonded to the principal chain of the polymer directly or through a methylene group) is remarkably low.

Accordingly, chelating agents useful in various utilization fields, namely, compounds which have water solubility, excellent inorganic-particle dispersibility and high scavengeability to heavy metals and can scavenge a large amount of metal ions per unit weight of the compounds, are desired.

SUMMARY OF THE INVENTION

A. Objects of the Invention

It is an object of the present invention to provide a water-soluble monomer, which can be favorably used as a starting-material for the above-mentioned compound with the excellent ability, and a production process therefor.

Furthermore, it is another object of the present invention to provide a chelating agent useful in various utilization fields, namely, a water-soluble polymer, which has water solubility, excellent inorganic-particle dispersibility and high scavengeability to heavy metals and can scavenge a large amount of metal ions per unit weight of the polymer, and a production process therefor and a composition containing the polymer.

B. Disclosure of the Invention (A water-soluble monomer)

A water-soluble monomer of the present invention has the following general formula (1):

wherein $R^1$ is H or $COOX^1$;

$R^2$ is H or $CH_2COOX^2$;

$R^3$ is $COOX^3$, OH or $CH_2COOX^3$;

$X^1$ is H, Na, K or $NH_4$;

$X^2$ is H, Na, K or $NH_4$;

$X^3$ is H, Na, K or $NH_4$;

$X^4$ is H, Na, K or $NH_4$;

and wherein $R^1$ and $R^2$ are not both H.

The water-soluble monomer may be prepared by a process comprising the step of reacting in an aqueous solution an amine compound and a cyclic acid anhydride, thus obtaining a water-soluble monomer having a carbon-carbon unsaturated double bond and a carboxyl group. The amine compound is at least one member selected from a group consisting of a primary amine with a carboxyl group and a primary amine salt with a partially or entirely neutralized carboxyl group. The cyclic acid anhydride includes a carbon-carbon unsaturated double bond.

(A process for producing a water-soluble monomer)

A process of the present invention for producing a water-soluble monomer having a carbon-carbon unsaturated double bond and a carboxyl group comprises the step of reacting in an aqueous solution an amine compound and a cyclic acid anhydride, thus obtaining the water-soluble monomer having the carbon-carbon unsaturated double bond and the carboxyl group. The amine compound is at least one member selected from a group consisting of a primary amine with a carboxyl group and a primary amine salt with a partially or entirely neutralized carboxyl group. The cyclic acid anhydride includes a carbon-carbon unsaturated double bond.

The water-soluble monomer that is obtained by the above-mentioned process of the present invention may be:

wherein $R^1$ is H or $COOX^1$;
$R^2$ is H or $CH_2COOX^2$;
$R^3$ is $COOX^3$, OH or $CH_2COOX^3$;
$X^1$ is H, Na, K or $NH_4$;
$X^2$ is H, Na, K or $NH_4$;
$X^3$ is H, Na, K or $NH_4$;
$X^4$ is H, Na, K or $NH_4$;
and wherein $R^1$ and $R^2$ are not both H.

The acid anhydride may be maleic anhydride.

The process may further comprise the steps of minimizing hydrolysis of the cyclic acid anhydride and minimizing Michael addition of the amine compound to the unsaturated double bond.

The amine compound may be dissolved in the aqueous solution, to which the cyclic acid anhydride may be then added.

The process may further comprise the step of maintaining the temperature of the aqueous solution between about 10° C. and about 0° C.

The aqueous solution may include a pH of between about 8 and about 13.

The total amount of the amine compound and the cyclic acid anhydride may be about 30% by weight, in terms of solid content, of the aqueous solution.

(A water-soluble polymer)

A water-soluble polymer of the present invention has a weight-average molecular weight of about 800 to about 8,000,000 and a structural unit having the following general formula (2):

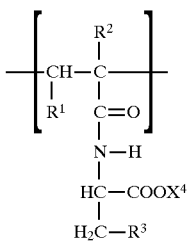

(2)

wherein
$R^1$ is H or $COOX^1$;
$R^2$ is H or $CH_2COOX^2$;
$R^3$ is $COOX^3$, OH or $CH_2COOX^3$;
$X^1$ is H, Na, K or $NH_4$;
$X^2$ is H, Na, K or $NH_4$;
$X^3$ is H, Na, K or $NH_4$;
$X^4$ is H, Na, K or $NH_4$;
and wherein $R^1$ and $R^2$ are not both H.

The structural unit may be in the polymer in the range of about 1 to about 100 mol %.

The weight-average molecular weight of the polymer may be in a range from about 1,000 to about 20,000.

The water-soluble polymer may be prepared by a process comprising the step of polymerizing in an aqueous medium a monomer including a compound having the following general formula (1):

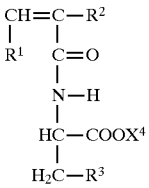

(1)

wherein
$R^1$ is H or $COOX^1$;
$R^2$ is H or $CH_2COOX^2$;
$R^3$ is $COOX^3$, OH or $CH_2COOX^3$;
$X^1$ is H, Na, K or $NH_4$;
$X^2$ is H, Na, K or $NH_4$;
$X^3$ is H, Na, K or $NH_4$;
$X^4$ is H, Na, K or $NH_4$;
and wherein $R^1$ and $R^2$ are not both H.

(A process for producing a water-soluble polymer)

A process of the present invention for producing a water-soluble polymer comprises the step of polymerizing in an aqueous medium a monomer including a compound having the following general formula (1):

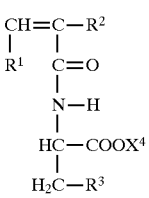

(1)

wherein
$R^1$ is H or $COOX^1$;
$R^2$ is H or $CH_2COOX^2$;
$R^3$ is $COOX^3$, OH or $CH_2COOX^3$;
$X^1$ is H, Na, K or $NH_4$;
$X^2$ is H, Na, K or $NH_4$;
$X^3$ is H, Na, K or $NH_4$;
$X^4$ is H, Na, K or $NH_4$;
and wherein $R^1$ and $R^2$ are not both H.

(A water-soluble compound)

A water-soluble compound of the present invention is selected from the group of compounds consisting of a water-soluble monomer compound having the general formula (1) below and a water-soluble polymer compound having the general formula (2) below.

General formula (1) showing the water-soluble monomer compound is:

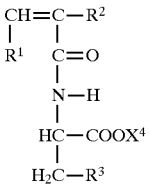

(1)

wherein
$R^1$ of the monomer compound is H or $COOX^1$;
$R^2$ of the monomer compound is H or $CH_2COOX^2$;
$R^3$ of the monomer compound is $COOX^3$, OH or $CH_2COOX^3$;
$X^1$ of the monomer compound is H, Na, K or $NH_4$;
$X^2$ of the monomer compound is H, Na, K or $NH_4$;
$X^3$ of the monomer compound is H, Na, K or $NH_4$;

$X^4$ of the monomer compound is H, Na, K or $NH_4$;
and wherein $R^1$ of the monomer compound and $R^2$ of the monomer compound are not both H.

The water-soluble polymer compound has a weight-average molecular weight of about 800 to about 8,000,000 and a structural unit having the following general formula (2):

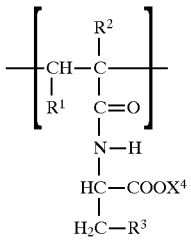
(2)

wherein
$R^1$ of the polymer compound is H or $COOX^1$;
$R^2$ of the polymer compound is H or $CH_2COOX^2$;
$R^3$ of the polymer compound is $COOX^3$, OH or $CH_2COOX^3$;
$X^1$ of the polymer compound is H, Na, K or $NH_4$;
$X^2$ of the polymer compound is H, Na, K or $NH_4$;
$X^3$ of the polymer compound is H, Na, K or $NH_4$;
$X^4$ of the polymer compound is H, Na, K or $NH_4$;
and wherein $R^1$ of the polymer compound and $R^2$ of the polymer compound are not both H.

(A detergent composition)

A detergent composition of the present invention comprises a water-soluble polymer having a weight-average molecular weight of about 800 to about 8,000,000 and a structural unit having the following general formula (2):

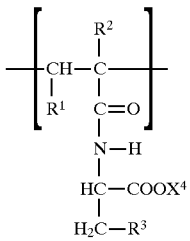
(2)

wherein
$R^1$ is H or $COOX^1$;
$R^2$ is H or $CH_2COOX^2$;
$R^3$ is $COOX^3$, OH or $CH_2COOX^3$;
$X^1$ is H, Na, K or $NH_4$;
$X^2$ is H, Na, K or $NH_4$;
$X^3$ is H, Na, K or $NH_4$;
$X^4$ is H, Na, K or $NH_4$;
and wherein $R^1$ and $R^2$ are not both H;
and with the detergent composition further comprising a surfactant.

The weight-average molecular weight of the water-soluble polymer included in the detergent composition may be in a range from about 1,000 to about 20,000.

The water-soluble polymer included in the detergent composition may be prepared by a process comprising the step of polymerizing in an aqueous medium a monomer including a compound having the following general formula (1):

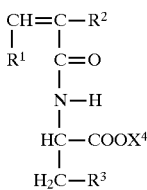
(1)

wherein
$R^1$ is H or $COOX^1$;
$R^2$ is H or $CH_2COOX^2$;
$R^3$ is $COOX^3$, OH or $CH_2COOX^3$;
$X^1$ is H, Na, K or $NH_4$;
$X^2$ is H, Na, K or $NH_4$;
$X^3$ is H, Na, K or $NH_4$;
$X^4$ is H, Na, K or $NH_4$;
and wherein $R^1$ and $R^2$ are not both H.

These and other objects and the advantages of the present invention will be more fully apparent from the following detailed disclosure.

DETAILED DESCRIPTION OF THE INVENTION

The present inventors worked diligently to solve the above-mentioned problems and encountered some surprising solutions to provide a water-soluble monomer, which is favorably used as a starting-material for the above-mentioned compound with the excellent ability, and a production process therefor. As a result, they have completed the present invention by finding that a monomer having a specific structure shown by the above-mentioned general formula (1) can be favorably used as a starting-material for producing the above-mentioned compound with the excellent ability, which compound is a polymer that has water solubility, excellent inorganic-particle dispersibility and high scavengeability to heavy metals and can scavenge a large amount of metal ions per unit weight of the polymer.

Furthermore, the present inventors worked diligently to solve the above-mentioned problems and encountered some surprising solutions. As a result, they have completed the present invention by finding that a polymer having a specific structural unit shown by the above-mentioned general formula (2) has water solubility, excellent inorganic-particle dispersibility and high scavengeability to heavy metals and can scavenge a large amount of metal ions per unit weight of the polymer, and that a composition containing this polymer can favorably be used, for example, as a detergent composition, an inorganic-pigment dispersant, a fiber-treating agent, a water-treating agent, or a wood pulp-bleaching assistant.

[Water-soluble monomer]

The water-soluble monomer of the present invention is a compound in which $R^1$, $R^2$, and $R^3$ in the aforementioned general formula (1) are as follows:
(i) $R^1$=$COOX^1$, $R^2$=H, $R^3$=$COOX^3$;
(ii) $R^1$=$COOX^1$, $R^2$=H, $R^3$=OH;
(iii) $R^1$=$COOX^1$, $R^2$=H, $R^3$=$CH_2COOX^3$;
(iv) $R^1$=H, $R^2$=$CH_2COOX^2$, $R^3$=$COOX^3$;
(v) $R^1$=H, $R^2$=$CH_2COOX^2$, $R^3$=OH;
(vi) $R^1$=H, $R^2$=$CH_2COOX^2$, $R^3$=$CH_2COOX^3$;
(vii) $R^1$=$COOX^1$, $R^2$=$CH_2COOX^2$, $R^3$=$COOX^3$;
(viii) $R^1$=$COOX^1$, $R^2$=$CH_2COOX^2$, $R^3$=OH; or
(ix) $R^1$=$COOX^1$, $R^2$=$CH_2COOX^2$, $R^3$=$CH_2COOX^3$.
In any of the compounds (i) to (ix), any of $X^1$, $X^2$, $X^3$, and $X^4$ can be H, Na, K or $NH_4$ independently of each other.

The water-soluble monomer of the present invention can be used as a starting-material for chelating agents useful in various utilization fields, namely, as a favorable starting-material for polymers which are compounds that have water solubility, excellent inorganic-particle dispersibility and high scavengeability to heavy metals and can scavenge a large amount of metal ions per unit weight of the compounds.

[Process for producing a water-soluble monomer]

In the production process of the present invention, a water-soluble monomer having a carbon-carbon unsaturated double bond and a carboxyl group is obtained by reacting an amine compound and a cyclic acid anhydride in an aqueous solution.

The amine compound is at least one member selected from a group consisting of a primary amine with a carboxyl group (which may simply be referred to as "primary amine" hereinafter) and a primary amine salt with a partially or entirely neutralized carboxyl group (which may simply be referred to as "primary amine salt" hereinafter). There is no especial limitation in the primary amine, but its examples are asparagic acid, serine, glutamic acid, alanine, phenylalanine. Examples of the primary amine salt are compounds having structures in which a carboxyl group moiety of the above-mentioned primary amine has partially or entirely formed its sodium salt, potassium salt, ammonium salt, organic amine salt, or at least one member selected from a group consisting of mixtures of at least two of these salts. Each of the primary amine and the primary amine salt may be used alone or in combinations of at least two thereof.

As to the cyclic acid anhydride, such having a carbon-carbon unsaturated double bond is used, and there is no especial limitation thereof, provided that it is an anhydride of an unsaturated polycarboxylic acid such as an unsaturated di- or tricarboxylic acid. Examples of the cyclic acid anhydride are maleic anhydride, itaconic anhydride, aconitic anhydride, 1-propene-1,2-dicarboxylic acid anhydride. The acid anhydride may be used alone or in combinations of at least two thereof. From a standpoint of economical availability, maleic anhydride is the most preferable of the acid anhydrides.

Of the above-exemplified compounds, sodium asparagate is particularly preferable as the primary amine salt, and maleic anhydride is particularly preferable as the acid anhydride. In an amidation reaction between sodium asparagate and maleic anhydride, a water-soluble monomer is obtained in very high yield, and properties of a polymer that is produced from this water-soluble monomer are very excellent.

The reaction between the amine compound and the cyclic acid anhydride having a carbon-carbon unsaturated double bond is carried out in an aqueous solution. Reaction conditions are not especially limited, but the below-mentioned ones are favorable for inhibiting side reactions, such as, hydrolysis of the acid anhydride, Michael addition of the amine compound to the unsaturated double bond, for inhibiting hydrolysis of a product, namely, a water-soluble monomer, and for obtaining a water-soluble monomer in high yield.

Preferred is a condition where the aforementioned aqueous solution is basic and where the amine compound and the cyclic acid anhydride are allowed to react in the aqueous solution while cooled.

The reaction temperature is preferably about 25° C. or lower and most preferably about 10° C. or lower, because as the reaction temperature becomes higher, the hydrolysis of the acid anhydride and the Michael addition of the amine compound to the unsaturated double bond advance faster.

The reaction pH is preferably in a range of about 7 to about 13, most preferably, about 8 to about 13, in the basic region. The pH can be adjusted by adding, for example, an alkaline metal hydroxide (e.g. sodium hydroxide, potassium hydroxide) to water. The pH adjustment is preferably carried out before adding the acid anhydride. When the pH is less than 7, namely, falls into the acid region, the amino group falls into non-free state because it is converted into a cation thereof, and thus there is a possibility that the yield of the resultant water-soluble monomer might be very low. In addition, when a base is excessively present, the resultant water-soluble monomer is easily hydrolyzed and thereby decomposed into an amine compound and an unsaturated polycarboxylic acid (or a salt thereof). This unsaturated polycarboxylic acid (or a salt thereof) does not react with the amine compound in an aqueous solution, so there is a possibility that the yield of the water-soluble monomer might be very low.

More preferred is a condition where the cyclic acid anhydride is gradually (preferably over a period of about 10 minutes or longer, most preferably about 30 minutes or longer) and continuously or intermittently and quantitatively added into an aqueous solution in which the amine compound is dissolved and which has a pH of about 7 to about 13 and a cooled temperature of about 25° C. or lower (or a pH of about 7 to about 13 and a cooled temperature of about 10° C. or lower, or a pH of about 8 to about 13 and a cooled temperature of about 25° C. or lower, or a pH of about 8 to about 13 and a cooled temperature of about 10° C. or lower, which parameters become more favorable in this order) while stirred. In the case where the acid anhydride followed by the amine compound is added to water, or where the acid anhydride is added to water at the same time as the amine compound, or where the entirety of the acid anhydride is added into an aqueous amine compound solution of pH about 7 to about 13 and about 25° C. or lower over a period shorter than about 10 minutes, there is a possibility that the acid anhydride might easily be hydrolyzed to greatly lower the yield of the resultant water-soluble monomer.

The reaction concentration is not especially limited, but a high one is preferable for inhibiting the hydrolysis of the acid anhydride to thereby promote the reaction, and the total amount of the amine compound and the cyclic acid anhydride is preferably about 30% by weight or more, and most preferably about 40% by weight or more, in terms of solid content, of the aqueous solution.

The ratio between the amine compound and the cyclic acid anhydride which are added water may be selected optionally.

If the acid anhydride is added in excess of the amine compound, the conversion of the amine compound can be increased to or near 100%. That the acid anhydride is added in excess of the amine compound means that the acid anhydride is added more than an equivalent molar amount of the amine compound. The excess of the acid anhydride can be selected optionally. When the acid anhydride is used excessively, the resultant reaction mixture contains a produced water-soluble monomer and the residue of the acid anhydride. This residue may be either removed from or allowed to remain in the reaction mixture. If the reaction mixture containing the acid anhydride is used for polymerization, a copolymer of the water-soluble monomer and the acid anhydride will produce.

In addition, if the amine compound is beforehand dissolved into water in excess of the acid anhydride that will be added thereafter, the conversion of the acid anhydride can be increased to or near 100%. That the amine compound is dissolved in excess of the acid anhydride means that the amine compound is dissolved more than an equivalent molar amount of the acid anhydride. The excess of the amine compound can be selected optionally. When the amine compound is used excessively, the resultant reaction mixture contains a produced water-soluble monomer and the residue of the amine compound. This residue may be either removed from or allowed to remain in the reaction mixture. In either case, if the reaction mixture in which no or almost no acid anhydride remains and which contains the resultant water-soluble monomer is used for polymerization, a homopolymer of the water-soluble monomer can be produced. The excessive amine compound can be removed from the resultant polymerization reaction mixture by conventional methods for removing amine compounds, such as, dialysis, after the production of the polymer.

The substituents $X^1$, $X^2$, $X^3$, and $X^4$ in the aforementioned general formula (1) consist of H, Na, K or $NH_4$ independently of each other. For example, a reaction mixture which is obtained from a reaction between the amine compound and the acid anhydride contains a water-soluble monomer in which any of the substituents $X^1$, $X^2$, $X^3$, and $X^4$ is H. If an aqueous solution of sodium hydroxide, potassium hydroxide, or ammonia is added and mixed into the reaction mixture, a partially or entirely neutralized water-soluble monomer can easily be obtained in which the substituents $X^1$, $X^2$, $X^3$, and $X^4$ consist of Na, K or $NH_4$ independently of each other. However, a treatment method for converting the substituents is not limited to those mentioned above.

Combinations of the amine compound and the cyclic acid anhydride which are used for producing the above-mentioned compounds (i) to (ix) are as follows:

Amine compound/cyclic acid anhydride
Compound (i): asparagic acid/maleic anhydride
Compound (ii): serine/maleic anhydride
Compound (iii): glutamic acid/maleic anhydride
Compound (iv): asparagic acid/itaconic anhydride
Compound (v): serine/itaconic anhydride
Compound (vi): glutamic acid/itaconic anhydride
Compound (vii): asparagic acid/aconitic anhydride
Compound (viii): serine/aconitic anhydride
Compound (ix): glutamic acid/aconitic anhydride.

Both the water-soluble monomer of the present invention and that which has been produced by the present invention process can form a homo- or co-polymer by conventional radical polymerization methods. In forming a copolymer, two or more of the water-soluble monomers can be used in combination, or one or more of the water-soluble monomers and one or more conventional monoethylenically unsaturated monomers can be used in combination. The resultant homo- or co-polymer contains a monomer unit derived from the water-soluble monomer, has a carboxyl group bonded to a carbon atom of the principal chain of the polymer directly or through a methylene group, and further has a carboxyl group at a site distant from the principal chain of the polymer. Therefore this polymer has a high carboxyl group density, in which the latter carboxyl group can freely rotate.

[Water-soluble polymer]

The water-soluble polymer of the present invention has a structural unit shown by the above-mentioned general formula (2). The content of the structural unit of the above-mentioned general formula (2) in the polymer is, for example, in a range of about 0.1 to about 100 mol %. If the content is in this range, at least one of the abilities of the polymer (the water solubility, the inorganic-particle dispersibility, the scavengeability to heavy metals, and the level of scavenging metal ions per unit weight of the polymer) is superior. From a viewpoint of achieving the superiority of at least one of these abilities of the polymer, the content of the structural unit of the general formula (2) is preferably in a range of about 1 to about 100 mol %, more preferably in a range of about 5 to about 100 mol %, and most preferably in a range of about 10 to about 40 mol %. The general formula (2) structural unit content of about 10 to about 40 mol % enhances the performance of the polymer particularly when the polymer is used for the later-mentioned detergent composition. The balance of the entire structural units of the polymer is a structural unit derived from the later-mentioned monomer (b).

The water-soluble polymer of the present invention has a structural unit in which $R^1$, $R^2$, and $R^3$ in the general formula (2) are as follows:
(i) $R^1$=$COOX^1$, $R^2$=H, $R^3$=$COOX^3$;
(ii) $R^1$=$COOX^1$, $R^2$=H, $R^3$=OH;
(iii) $R^1$=$COOX^1$, $R^2$=H, $R^3$=$CH_2COOX^3$;
(iv) $R^1$=H, $R^2$=$CH_2COOX^2$, $R^3$=$COOX^3$;
(v) $R^1$=H, $R^2$=$CH_2COOX^2$, $R^3$=OH;
(vi) $R^1$=H, $R^2$=$CH_2COOX^2$, $R^3$=$CH_2COOX^3$;
(vii) $R^1$=$COOX^1$, $R^2$=$CH_2COOX^2$, $R^3$=$COOX^3$;
(viii) $R^1$=$COOX^1$, $R^2$=$CH_2COOX^2$, $R^3$=OH; or
(ix) $R^1$=$COOX^1$, $R^2$=$CH_2COOX^2$, $R^3$=$CH_2COOX^3$.

In any of structural units (i) to (ix) above, any of $X^1$, $X^2$, $X^3$, and $X^4$ can be H, Na, K or $NH_4$ independently of each other.

If the weight-average molecular weight of the water-soluble polymer of the present invention is in a range of about 800 to about 8,000,000, at least one of the abilities of the polymer (the water solubility, the inorganic-particle dispersibility, the scavengeability to heavy metals, and the level of scavenging metal ions per unit weight of the polymer) is superior. From a viewpoint of achieving the superiority of at least one of these abilities of the polymer, the weight-average molecular weight of the polymer is preferably in a range of about 800 to about 100,000 and more preferably in a range of about 1,000 to about 20,000. Particularly where this polymer is used as a detergent builder for a detergent composition, the weight-average molecular weight of the polymer is preferably in a range of about 800 to about 100,000 and more preferably in a range of about 1,000 to about 20,000.

The water-soluble polymer of the present invention, for example, can be produced by:

(1) the later-mentioned process for producing a water-soluble polymer;

(2) a process in which a polymer having a cyclic acid anhydride is produced by conventional methods, and a ring-opening amidation reaction between this polymer and a primary amine containing a carboxyl group is then carried out by conventional methods; or (3) a process in which a polymer containing a structure derived from a monoethylenically unsaturated polycarboxylic acid monoester is produced by conventional methods, and a trans-esterification-amidation reaction between this polymer and a primary amine containing a carboxyl group is then carried out by conventional methods.

Of processes (1) to (3) above, process (1) is preferable.

[Process for producing a water-soluble polymer]

The process for producing a water-soluble polymer, according to the present invention, includes a step of polymerizing a monomer including a compound shown by the aforementioned general formula (1) (hereinafter this compound is referred to as "monomer (a)").

Monomer (a) is a water-soluble monomer having two types of carboxyl groups, namely, a carboxyl group which is bonded to a carbon-carbon unsaturated double bond directly or through a methylene group and therefore located near the double bond, and a carboxyl group which is located at a site distant from the double bond. This monomer, for example, can be obtained by a production process including a step of reacting an amine compound and a cyclic acid anhydride (hereinafter, this process is referred to as "production process A"). Details thereof are mentioned previously.

In production process A, because the amine compound and the cyclic acid anhydride having a carbon-carbon unsaturated double bond are reacted in an aqueous solution, a water-soluble ethylenically unsaturated monomer (a) is produced which has a carboxyl group bonded to a carbon atom of a carbon-carbon unsaturated double bond directly or through a methylene group as well as a carboxyl group at a site distant from a carbon atom of a carbon-carbon unsaturated double bond and therefore has a high carboxyl group density overall.

The polymer of the present invention, for example, can easily be produced by polymerizing monomer (a) alone or copolymerizing monomer (a) with another ethylenically unsaturated monomer (hereinafter referred to as "monomer (b)") which is copolymerizable with monomer (a).

Because the resultant homo- or co-polymer has a carboxyl group bonded to a carbon atom of its principal chain directly or through a methylene group, this polymer has a high carboxyl group density near its principal chain. In addition, because a carboxyl group is also present at a site distant from the principal chain of this polymer, this carboxyl group can freely rotate.

Monomer (b) preferably has water solubility and more preferably has a solubility of about 5 g or more per 100 g of water at 100° C.

The ratio between monomers (a) and (b) which are copolymerized is not especially limited, but the molar ratio of monomer (a) to the total of both monomers is, for example, not less than 1/100, but less than 1.

Specific examples of monomer (b) are not especially limited, but are as follows: unsaturated monocarboxylic acids and salts thereof, such as, acrylic acid, methacrylic acid, α-hydroxyacrylic acid, crotonic acid; unsaturated polycarboxylic acids and salts thereof, such as, maleic acid, maleic anhydride, citraconic acid, aconitic acid; and vinyl acetate.

In addition, other examples of monomer (b) are hydroxyl group-containing unsaturated compounds shown by the following general formula (3):

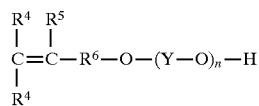

(wherein: $R^4$ and $R^5$ denote a hydrogen atom or a —$CH_3$ group, but both $R^4$ and $R^5$ are not —$CH_3$; $R^6$ denotes —$CH_2$—, —$(CH_2)_2$—, or —$C(CH_3)_2$—; the number of the carbon atoms contained in $R^4$, $R^5$ and $R^6$ is 3 in total; Y denotes a alkylene group with 2 to 3 carbon atoms; n is an integer of 0 to 100), such as, 3-methyl-3-buten-1-ol (which may be called "isoprenol"), 3-methyl-2-buten-1-ol (which may be called "prenol"), 2-methyl-3-buten-2-ol (which may be called "isoprene alcohol"), and compounds obtained by adding 1–100 mol of either or both of ethylene- and propylene oxide to 1 mol of the above-mentioned compounds.

Furthermore, other examples of monomer (b) are compounds shown by the following general formula (4):

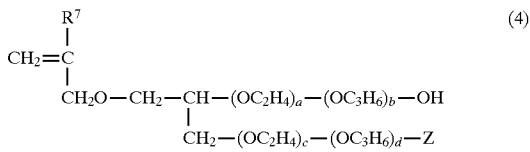

(wherein: $R^7$ denotes a hydrogen atom or a —$CH_3$ group; a, b, c, and d are integers of 0 to 100; a+b+c+d=0 to 100; the bonding order of —$OC_2H_4$— and —$OC_3H_6$— is not limited; in the case of c+d=0, Z denotes a hydroxyl group, a sulfonic acid group, or a phosphorous or phosphoric acid group; in the case of c+d=1 to 100, Z denotes a hydroxyl group), such as: 3-allyloxy-2-hydroxypropanesulfonic acid and salts thereof; unsaturated (meth)allyl ether-based compounds, e.g., glycerol monoallyl ether and compounds obtained by adding 1–100 mol of either or both of ethylene- and propylene oxide to 1 mol of glycerol monoallyl ether; unsaturated sulfonic acid group-containing compounds and salts thereof, e.g., vinylsulfonic acid, allylsulfonic acid, methallylsulfonic acid, styrenesulfonic acid, 2-acrylamide-2-methylpropanesulfonic acid, sulfoethyl(meth)acrylate, sulfopropyl(meth)acrylate, 2-hydroxysulfopropyl(meth) acrylate, sulfoethylmaleimide; terminal alkyl group-containing ester-based unsaturated compounds, e.g., esters from alcohols (obtained by adding 1–100 mol of either or both of ethylene- and propylene oxide to 1 mol of alkyl alcohols with 1–20 carbon atoms) and monocarboxylic acids (e.g. (meth)acrylic acid, crotonic acid), monoesters and salts thereof and diesters from polycarboxylic acids (e.g. maleic acid, fumaric acid, itaconic acid, citraconic acid, aconitic acid) and ethylene oxide- and/or propylene oxide adducts of the above-mentioned alkyl alcohols; ester-based unsaturated compounds, e.g., ester-based compounds obtained by adding 1–100 mol of either or both of ethylene- and propylene oxide to 1 mol of unsaturated carboxylic acids (e.g. (meth) acrylic acid, crotonic acid), and monoester-based compounds and salts thereof and diester-based compounds obtained by adding 1–100 mol of either or both of ethylene- and propylene oxide to 1 mol of unsaturated polycarboxylic acids (e.g. maleic acid, fumaric acid, itaconic acid, citraconic acid, aconitic acid).

Monomer (b) may be used alone or in combinations of at least two thereof. Of the above-exemplified compounds, the use of either or both of (meth)acrylic acid (salt) and maleic acid (salt) is particularly preferred from a standpoint of their polymerization reactivity or properties of the resultant polymer.

In the polymerization reaction for producing a polymer of the present invention, a polymerization initiator may be used, if necessary. Examples of usable polymerization initiators are as follows: hydrogen peroxide; persulfates, such as, ammonium persulfate, sodium persulfate, potassium persulfate; 2,2'-azobis(2-amidinopropane)hydrochlorate; azo compounds, such as, 4,4'-azobis-4-cyanovaleric acid, azobisisobutyronitrile, 2,2'-azobis(4-methoxy-2,4-dimethylvaleronitrile); organic peroxides, such as, benzoyl peroxide, lauroyl peroxide, peracetic acid, persuccinic acid, di-tert-butyl peroxide, tert-butyl hydroperoxide, cumene hydroperoxide; but there is no especial limitation. The polymerization initiator may be used alone or in combinations of at least two thereof.

Conditions for the polymerization reaction are, for example, those where the reaction temperature is about 100° C. and the reaction duration is about 180 minutes, but there is no especial limitation and the conditions may be set appropriately depending upon the type or amount of the monomer, catalyst, or aqueous medium. In addition, the reaction pressure is not especially limited, and it may be any of normal (atmospheric), reduced, or increased ones.

The pH during the polymerization reaction can be an optional value. However, monomer (a), which is a starting material, has an amide bond. Thus, for the purpose of inhibiting the hydrolysis of this amide bond, the polymerization is preferably carried out under basic conditions and more preferably under conditions where the pH is adjusted to between about 8 and about 10. The basic compound which is used for the pH adjustment during polymerization is not especially limited, but examples thereof are as follows: hydroxides or carbonates of alkaline metals such as sodium, potassium, and lithium; ammonia; alkylamines, such as, monomethylamine, diethylamine, trimethylamine, monoethylamine, dimethylamine, triethylamine; alkanolamines, such as, monoethanolamine, diethanolamine, triethanolamine, isopropanolamine, secondary-butanolamine; and pyridine. The basic compound may be used alone or in combinations of at least two thereof.

It is preferable that the monomer is polymerized in the presence of a polyvalent metal ion, because, in such a way, the amount of the monomer, remaining in the reaction solution after the completion of the polymerization, can be decreased, so that the molecular weight distribution of the resultant polymer can be narrowed. Usable polyvalent metal ions are not especially limited, but examples thereof are iron ions, vanadium atom-containing ions, and copper ions. Of these exemplified ions, particularly $Fe^{3+}$, $Fe^{2+}$, $Cu^+$, $Cu^{2+}$, $V^{2+}$, $V^{3+}$, and $VO^{2+}$ are preferable, and $Fe^{3+}$, $Cu^{2+}$, and $VO^{2+}$ are more preferable. The polyvalent metal ion may be used alone or in combinations of at least two thereof.

The concentration of the polyvalent metal ion is preferably in a range of about 0.1 to about 100 ppm relative to the entirety of the reaction solution. In the case where the concentration is less than about 0.1 ppm, almost no effects as mentioned above can be obtained. In the case where the concentration is more than about 100 ppm, for example, a maleic acid-based copolymer obtained by copolymerizing a maleic acid-based monomer is colored and therefore cannot be utilized for uses such as detergent compositions. In addition, a polymer obtained by polymerization in the presence of a polyvalent metal ion is excellent with regard to the so-called iron particle settlement inhibitability, and therefore can favorably be utilized for uses such as detergent compositions.

The way to allow the polyvalent metal ion to be present in the reaction solution is not especially limited, but metal compounds or metals which can be ionized in the reaction solution may, for example, be added to the reaction solution. Examples of such metal compounds or metals are as follows: water-soluble metal salts, such as, vanadium oxytrichloride, vanadium trichloride, vanadium oxalate, vanadium sulfate, vanadic anhydride, ammonium metavanadate, ammonium hypo-vanadious sulfate [$(NH_4)_2SO_4 \cdot VSO_4 \cdot 6H_2O$], ammonium vanadious sulfate [$(NH_4)V(SO_4)_2 \cdot 12H_2O$], copper (II) acetate, copper (II) bromide, copper (II) acetylacetate, ammonium cupric chloride cuprous chloride, copper carbonate, copper (II) chloride, copper (II) citrate, copper (II) formate, copper (II) hydroxide, copper nitrate, copper naphthenate, copper (II) oleate, copper maleate, copper phosphate, copper (II) sulfate, cuprous chloride, copper (I) cyanide, copper iodide, copper (I) oxide, copper thiocyanate, iron acetylacetonate, iron ammonium citrate, ferric ammonium oxalate, ferrous ammonium sulfate, ferric ammonium sulfate, iron citrate, iron fumarate, iron maleate, ferrous lactate, ferric nitrate, iron pentacarbonyl, ferric phosphate, ferric pyrophosphate; metal oxides, such as, vanadium pentaoxide, copper (II) oxide, ferrous oxide, ferric oxide; metal sulfides, such as, copper (II) sulfide, iron sulfide; copper powder, iron powder; but there is no especial limitation.

It is preferable that the above-mentioned polymerization reaction is carried out in an aqueous medium, from a standpoint of the convenience in that the reaction solution containing the resultant polymer can intactly be used for a composition containing a polymer of the present invention, because this composition is mainly used in a water system, and that when this composition is used as a powdered detergent composition, it is unnecessary to recover solvents from the composition after its preparation, and the composition can easily be dried, and in addition, from a standpoint of economical merits. Specific examples of usable aqueous media are as follows: water; hydrophilic solvents such as alcohols (e.g. methanol, ethanol); but there is no especial limitation. The aqueous medium may be alone or in combinations of at least two thereof.

[Use]

Next, the composition, according to the present invention, is explained.

Because this composition contains the polymer with the structural unit shown by the general formula (2) (hereinafter this polymer referred to as polymer A), it can favorably be used, for example, as a detergent composition, a fiber-treating agent, an inorganic-pigment dispersant, a water-treating agent, a wood pulp-bleaching assistant. Hereinafter, each of these uses is explained in detail.

When the composition of the present invention is a detergent composition, this detergent composition contains polymer A, a surfactant and, as needed, for example, an enzyme. Preferable examples of the surfactant are anionic surfactants, nonionic surfactants, amphoteric surfactants, and cationic surfactants.

The content of polymer A in the detergent composition is preferably in a range of about 0.5 to about 80% by weight, more preferably, about 1 to about 30% by weight. In the case where the content of polymer A is too little, there is a possibility that effects from addition of polymer A might not sufficiently emerge, and that the enhancement of the washing power therefore could not be expected. In the case where the content of polymer A is too much, there is a possibility that effects of the washing power enhancement rewarding the amount of polymer A being added might be seen no longer, which is economically disadvantageous.

The anionic surfactant is not especially limited, but examples thereof are alkylbenzenesulfonic acid salts, alkyl ether sulfuric acid salts, alkenyl ether sulfuric acid salts, alkylsulfuric acid salts, alkenylsulfuric acid salts, $\alpha$-olefinsulfonic acid salts, $\alpha$-sulfofatty acids, $\alpha$-sulfofatty acid ester salts, alkanesulfonic acid salts, saturated or unsaturated fatty acid salts, alkyl ether carboxylic acid salts, alkenyl ether carboxylic acid salts, amino acid type surfactants, N-acylamino acid type surfactants, alkylphosphoric acid esters or salts thereof, alkenylphosphoric acid esters or salts thereof.

The nonionic surfactant is not especially limited, but examples thereof are polyoxyalkylene alkyl ethers, polyoxyalkylene alkenyl ethers, polyoxyethylene alkyl phenyl ethers, higher fatty acid alkanolamides or alkylene oxide adducts thereof, sucrose fatty acid esters, alkyl glycoxides, fatty acid glycerol monoesters, alkylamine oxides.

The amphoteric surfactant is not especially limited, but examples thereof are carboxy type or sulfobetaine type amphoteric surfactants.

The cationic surfactant is not especially limited, but examples thereof are quaternary ammonium salts.

The content of the surfactant in the detergent composition is preferably in a range of about 5 to about 70% by weight, more preferably, about 20 to about 60% by weight. In the case where the content of the surfactant is too little, there is a possibility that the washing power, particularly, to oily dirt, might not be sufficient. In the case where the content of the surfactant is too much, there is a possibility that the balance between the surfactant and polymer A might be broken, and that the surfactant therefore might not contribute any longer to the washing power enhancement rewarding the amount of polymer A being added.

The enzyme which can be combined with the detergent composition is not especially limited, but examples thereof are protease, lipase, cellulase. Particularly, protease, alkali lipase, and alkali cellulase, which are high active in alkali washing liquids, are preferable. The content of the enzyme in the detergent composition is preferably in a range of about 0.01 to about 5% by weight. In the case where the amount of the enzyme being combined deviates from this range, there is a possibility that the balance between the enzyme and the surfactant might be broken, and that the washing power therefore could not be enhanced.

Upon need, the detergent composition can further contain components which are commonly used for conventional detergent compositions, for example, conventional alkali builders, chelate builders, reattachment inhibitors, fluorescent agents, bleachers, and perfumes, and in addition, dispersion media such as solubilizers which are used for liquid detergent compositions. The alkali builder is not especially limited, but examples thereof are silicates, carbonates, sulfates. The chelate builder is not especially limited, but examples thereof are diglycolic acid, oxycarboxylates, EDTA (ethylenediaminetetraacetate), DTPA (diethylenetriaminehexaacetate), citric acid. In addition, zeolite also may be added to the detergent composition to thereby enhance its washing power.

When the composition of the present invention is a fiber-treating agent, this fiber-treating agent contains: at least one component selected from a group consisting of dyes, peroxides, and surfactants; and polymer A. This fiber-treating agent can be used any of steps of scouring, dyeing, bleaching, and soaping in fiber treatment. The dyes, peroxides, and surfactants, which may be combined with polymer A, are not especially limited, but those which are used for conventional fiber-treating agents are available. The ratio of combination of the dyes, peroxides, and surfactants to polymer A is not especially limited. However, for example, when polymer A is a maleic acid-based copolymer, about 0.1 to about 100 parts by weight, per part by weight of polymer A, of the above-mentioned components, such as dyes, other than polymer A may be added to improve properties of fibers, such as, whiteness degree, color evenness, dyed-colorfastness degree. Fibers for which the above-mentioned fiber-treating agent can be used are not especially limited, but examples thereof are as follows: cellulose fibers, such as, cotton, hemp; chemical fibers, such as, nylon, polyester; animal fibers, such as, wool, silk; semisynthetic fibers, such as, rayon; and any fabric and blend thereof.

In the case where a fiber-treating agent containing a maleic acid-based copolymer as polymer A is used in the scouring process, it is preferable that the fiber-treating agent further contains alkali agents and surfactants. In addition, in the case where the fiber-treating agent containing a maleic acid-based copolymer as polymer A is used in the bleaching process, it is preferable that the fiber-treating agent further contains peroxides and silicic acid-based chemicals, such as sodium silicate, which are decomposition inhibitors for alkaline bleachers.

In the case where the composition of the present invention is an inorganic-pigment dispersant, this inorganic-pigment dispersant contains polymer A. Upon need, this inorganic-pigment dispersant, for example, may further contain an optional amount of at least one compound selected from a group consisting of: polymerized phosphoric acid and salts thereof, phosphonic acid and salts thereof, and polyvinyl alcohol and products modified by anionization thereof (where two or more compounds are selected, mixtures thereof are also available).

The above-mentioned inorganic-pigment dispersant displays good performance as a dispersant for inorganic pigments, such as, heavy or light calcium carbonate, clay, which are used for paper coating. For example, if a small amount of the inorganic-pigment dispersant is added to an inorganic pigment and then dispersed into water, highly concentrated inorganic pigment slurries (e.g. highly concentrated calcium carbonate slurries) can be produced which have a low viscosity, a high fluidity, and a good stability in that these properties do not change with time. The amount of the inorganic-pigment dispersant being used is preferably in a range of about 0.05 to about 2.0 parts by weight per 100 parts by weight of inorganic pigment. In the case where the amount of the inorganic-pigment dispersant is too small, sufficient dispersing effects might not be displayed. On the other hand, the use of too large an amount of the inorganic-pigment dispersant might be economically disadvantageous in that the improvement of the dispersing effects rewarding the amount might not be expected any longer.

In the case where the composition of the present invention is a water-treating agent, this water-treating agent contains polymer A. Upon need, this water-treating agent, for example, may further contain an optional amount of at least one compound selected from a group consisting of polymerized phosphoric acid salts, phosphonic acid salts, anticorrosive agents, slime controlling agents, and chelating agents (where two or more compounds are selected, mixtures thereof are also available). This water-treating agent is useful for inhibiting formation of scale in systems, such as, cooling water-circulating systems, boiler water-circulating systems, seawater desalination plants, pulp digesters, black liquor evaporators.

In the case where the composition of the present invention is a wood pulp-bleaching assistant, this wood pulp-bleaching assistant contains polymer A. This wood pulp-bleaching assistant may be used as a pretreatment agent or together with other components, such as, hydrogen peroxide, chlorine-based bleachers, ozone, in bleaching wood pulp.

(Advantages of the invention)

Because the water-soluble monomer of the present invention is shown by the aforementioned general formula (1), it can favorably be used as a monomer for producing a polymer which has carboxyl groups at both sites near and distant from its principal chain and in which the carboxyl groups are present in high density. Thus, if this water-soluble monomer is polymerized, a polymer can be produced which has water solubility, excellent inorganic-particle dispersibility and high scavengeability to heavy metals and can scavenge a large amount of metal ions per unit weight of the polymer, when compared with conventional chelating agents. This polymer can favorably be used for various purposes, such as, detergent compositions, inorganic-pigment dispersants, fiber-treating agents, water-treating agents, wood pulp-bleaching assistants.

In the process for producing a water-soluble monomer, relating to the present invention, because the aforementioned amine compound and the aforementioned cyclic acid anhydride are reacted in an aqueous solution, the amine compound is difficult to add to a carbon-carbon unsaturated double bond, and an imidation reaction is also difficult to occur. Therefore the water-soluble monomer shown by the aforementioned general formula (1) can easily be obtained.

Because the water-soluble polymer of the present invention has a structural unit, shown by the aforementioned general formula (2), and a weight-average molecular weight of about 800 to about 8,000,000, this polymer has a molecular structure containing many carboxyl groups which are bonded both directly and indirectly to the principal chain of the polymer. Therefore, this polymer has water solubility and, when compared with conventional chelating agents, this polymer has excellent inorganic-particle dispersibility and high scavengeability to heavy metals and can scavenge a large amount of metal ions per unit weight of the polymer. This polymer, for example, has excellent chelating and dispersing actions when compared with conventional chelating agents.

Because the process, according to the present invention, for producing a polymer includes the step of polymerizing a monomer including a compound shown by the aforementioned general formula (1), this process can easily provide the water-soluble polymer of the present invention.

The water-soluble polymer or the composition containing this polymer, according to the present invention, can favorably be used for various purposes, such as, detergent compositions, fiber-treating agents, inorganic-pigment dispersants, water-treating agents, wood pulp-bleaching assistants.

DETAILED DESCRIPTION OF THE PREFERRED EMBODIMENTS

Hereinafter, the present invention is illustrated by the following examples of some preferred embodiments in comparison with comparative examples not according to the invention. However, the present invention is not limited to these examples. In addition, in the examples, unless otherwise noted, the units "%" and "part(s)" denote those by weight.

EXAMPLE 1

First, a maleic acid-sodium asparagate monoamide matter (hereinafter referred to as "monomer (a1)") was synthesized as monomer (a) as follows. A mixture of 133 parts of DL-asparagic acid, 167 parts of a 48% aqueous sodium hydroxide solution, and 54.3 parts of ion-exchanged water was placed into a 4-necked flask of 500 ml in capacity equipped with a thermometer, a pH meter, and a stirrer. Next, while the contents of the flask were maintained at 10° C. or lower under stirred conditions, 98 parts of maleic anhydride was added into the flask over a period of 60 minutes by quantitative dropwise addition, when a 48% aqueous sodium hydroxide solution was appropriately added to maintain the pH of the aqueous reaction solution at 9 or more. After the addition of maleic anhydride had completed, the stirring of the reaction mixture was continued for 30 minutes while the reaction mixture was maintained at 10° C. or lower. After the reaction had completed, 56.7 parts of ion-exchanged water was added, and the pH of the reaction mixture was then adjusted to 11.5 with a 48% aqueous sodium hydroxide solution. As a result, an aqueous brown transparent solution was obtained. Then, water was removed from this solution to thereby obtain a powdered white solid substance.

This solid substance was identified by IR and $^1$H-NMR measurement. Results thereof are as follows:

IR (KBr method): 1700 cm$^{-1}$ (s) (CONHR)

$^1$H-NMR (solvent: D$_2$O):

δ 2.2–2.6 ppm (m, 2H, CH$_2$)

δ 4.2–4.4 ppm (m, 1H, NH—C$\underline{\text{H}}$)

δ 5.7–5.8 ppm (d, 1H, CH=)

δ 6.2–6.3 ppm (d, 1H, CH=)

The presence of an amide bond (CONHR) was confirmed from the IR measurement. In addition, from the $^1$H-NMR spectrum analysis, it could be confirmed that the above-mentioned product, obtained in Example 1, was a compound, namely, monomer (a1), shown by the following structural formula:

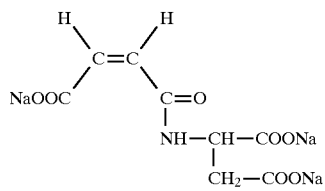

In addition, the solid content of the aqueous brown transparent solution was 36%. From an integral ratio of $^1$H-NMR peaks, the conversion of DL-asparagic acid was calculated as 86%, and that of maleic anhydride as 78%. A by-product was imidinosuccinic acid. The ratio by weight of their presence was (monomer (a1)):(DL-asparagic acid):(maleic acid):(by-product)=80:2:7:11 (any of which was a sodium salt thereof). Thus, the aqueous brown transparent solution contained monomer (a1).

Using this aqueous brown transparent solution, a polymer was synthesized in the following way. Two hundred and fifty parts of this solution (containing 71.2 parts of monomer (a1) and 6.2 parts of sodium maleate as monomer (b)) was placed into a 4-necked flask of 500 ml in capacity equipped with a thermometer, a stirrer, and a reflux condenser. After the solution was heated to its boiling point while stirred, 12.6 parts of a 35% aqueous hydrogen peroxide solution was continuously dropwise added into the flask over a period of 30 minutes under stirred conditions. Subsequently, 19.6 parts of a 15% aqueous sodium persulfate solution was continuously dropwise added into the flask under stirred conditions over a period of 70 minutes from the completion of the dropwise addition of the aqueous hydrogen peroxide solution. In parallel with this dropwise addition operation, 37.8 parts of a 80% aqueous solution of acrylic acid as monomer (b) was also continuously dropwise added into the aqueous reaction solution over a period of 90 minutes from the initiation of the dropwise addition of the aqueous hydrogen peroxide solution. After the dropwise addition of all materials had completed, the reaction solution was maintained at its boiling point for 60 minutes to carry out a polymerization reaction. In this reaction, the molar ratio of monomer (a1), sodium maleate, and acrylic acid was 34:6:60.

After the reaction had completed, the pH was adjusted to 8.5 with a 48% aqueous sodium hydroxide solution, thereby obtaining an aqueous brown transparent solution with a solid content of 45.5%. Next, a post-treatment of removing residual monomers and low molecular weight products was carried out to measure the composition ratio of and the weight-average molecular weight of the resultant polymer as follows. The resultant aqueous polymer solution was dialyzed over a period of 12 hours under a water flow using a dialysis membrane, SPECTRA-PORE 6 (made by IEDA TRADING Co.), with a differential molecular weight of 1,000, thereby obtaining an aqueous pale brown transparent solution, with a solid content of 4.5% and pH of 10.0, of a polymer (hereinafter referred to as "polymer (1)"). Then, the water content was removed from this solution to thereby obtain a white powder.

This white powder was measured by IR and $^1$H-NMR. Results thereof are as follows:

IR (KBr method): 1700 cm$^{-1}$ (s) (CONHR)
$^1$H-NMR (solvent: D$_2$O): δ 4–4.4 ppm (m, NH—C$\underline{H}$)

From the above-mentioned results, it was confirmed that an amide bond (CONHR) was present in the resultant polymer, and it was clear that monomer (a1) was introduced into polymer (1). In addition, from analysis of the integral ratio of proton in the $^1$H-NMR spectrum, it could be confirmed that polymer (1) was shown by the following structural formula:

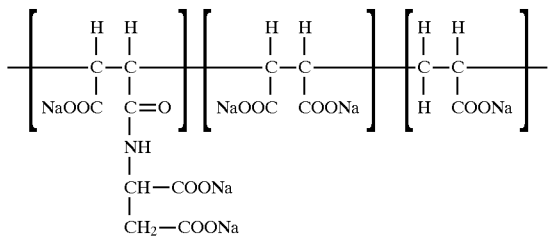

and contained a monomer (a1) structural unit, a sodium maleate structural unit, and a sodium acrylate structural unit in a molar ratio of 27:27:46.

In addition, the average molecular weight of polymer (1) was measured by gel permeation chromatography (hereinafter abbreviated as "GPC"), when Shodex GF-7MHQ (made by Showa Denko Co.) was used as the column, a 0.5% aqueous sodium phosphate solution (of which the pH was 7) as the eluent, and a sodium polyacrylate standard sample (made Sowa Kagaku Co.) as the molecular weight standard sample. Results provided a weight-average molecular weight (Mw) of 4,100. In this way, it could be confirmed that water-soluble polymer (1) could be synthesized.

EXAMPLE 2

First, a sodium salt of a maleic acid-L-serine monoamide matter (hereinafter referred to as "monomer (a2)") was synthesized as monomer (a) as follows. A mixture of 21 parts of L-serine, 16.7 parts of a 48% aqueous sodium hydroxide solution, and 13.1 parts of ion-exchanged water was placed into a 4-necked flask of 100 ml in capacity equipped with a thermometer, a pH meter, and a stirrer. Next, while the contents of the flask were maintained at 10° C. or lower under stirred conditions, 40 parts of maleic anhydride was added into the flask over a period of 60 minutes by quantitative dropwise addition (maleic anhydride was added excessively in this reaction, but the excess thereof was intactly used as monomer (b) for subsequent synthesis of a polymer), when a 48% aqueous sodium hydroxide solution was appropriately added to maintain the pH of the aqueous reaction solution at 9 or more. After the addition of maleic anhydride had completed, the stirring of the reaction mixture was continued for 30 minutes while the reaction mixture was maintained at 10° C. or lower. After the reaction had completed, 47 parts of ion-exchanged water was added, and the pH of the reaction mixture was then adjusted to 12.5 with a 48% aqueous sodium hydroxide solution. As a result, an aqueous colorless transparent solution with a solid content of 34.1% was obtained. Then, water was removed from this solution to thereby obtain a powdered white solid substance.

This solid substance was identified by IR and $^1$H-NMR measurement. Results thereof are as follows:

IR (KBr method): 1700 cm$^{-1}$ (s) (CONHR)
$^1$H-NMR (solvent: D$_2$O):
δ 3.6–3.8 ppm (m, 2H, C$\underline{H_2}$—OH)
δ 4.0 ppm (m, 1H, NH—C$\underline{H}$)
δ 5.8–5.9 ppm (d, 1H, CH=)
δ 6.2–6.3 ppm (d, 1H, CH=)

The presence of an amide bond (CONHR) was confirmed from the IR measurement. In addition, from the $^1$H-NMR spectrum analysis, it could be confirmed that the above-mentioned product, obtained in Example 2, was a compound, namely, monomer (a2), shown by the following structural formula:

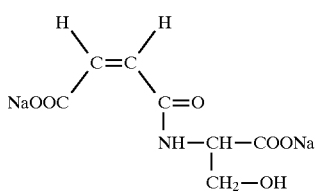

In addition, from an integral ratio of $^1$H-NMR peaks, the conversion of L-serine was calculated as 100%, and that of maleic anhydride as 51%. Any by-products were not formed. Accordingly, the ratio by weight of their presence was (monomer (a2)):(maleic acid)=62:38 (both of which are sodium salts thereof). Thus, the aqueous colorless transparent solution contained monomer (a2).

Using this aqueous colorless transparent solution, a polymer was synthesized as follows. One hundred parts of this solution (containing 20 parts of monomer (a2) and 13 parts of sodium maleate as monomer (b)) was placed into a 4-necked separable flask of 200 ml in capacity equipped with a thermometer, a stirrer, and a reflux condenser. After the solution was heated to its boiling point while stirred, 4.8 parts of a 35% aqueous hydrogen peroxide solution was continuously dropwise added into the flask over a period of 30 minutes under stirred conditions. Subsequently, 3.7 parts of a 15% aqueous sodium persulfate solution was continuously dropwise added into the flask under stirred conditions over a period of 70 minutes from the completion of the dropwise addition of the aqueous hydrogen peroxide solution. In parallel with this dropwise addition operation, 21.6 parts of a 80% aqueous solution of acrylic acid as monomer (b) was also continuously dropwise added into the aqueous reaction solution over a period of 90 minutes from the initiation of the dropwise addition of the aqueous hydrogen peroxide solution. After the dropwise addition of all materials had completed, the reaction solution was maintained at its boiling point for 60 minutes to carry out a polymerization reaction. In this reaction, the molar ratio of monomer (a2), sodium maleate, and acrylic acid was 20:20:60.

After the reaction had completed, 78 parts of ion-exchanged water was added, and the pH was then adjusted to 8.5 with a 48% aqueous sodium hydroxide solution, thereby obtaining an aqueous red brown transparent solution with a solid content of 24.7%. Next, a post-treatment of removing residual monomers and low molecular weight products from the resultant aqueous solution was carried out in the same way as of Example 1, thereby obtaining an aqueous pale brown transparent solution, with a solid content of 4.5% and pH of 10.0, of a polymer (hereinafter referred to as "polymer (2)"). Then, the water content was removed from this solution to thereby obtain a white powder.

This white powder was measured by IR and $^1$H-NMR. Results thereof are as follows:

IR (KBr method): 1700 cm$^{-1}$ (s) (CONHR)
$^1$H-NMR (solvent: D$_2$O): δ 4–4.4 ppm (m, NH—C$\underline{H}$)

From the above-mentioned rebolts, it was confirmed that an amide bond (CONHR) was present in the resultant polymer, and it was clear that monomer (a2) was introduced into polymer (2). In addition, from analysis of the integral ratio of proton in the $^1$H-NMR spectrum, it could be confirmed that polymer (2) was shown by the following structural formula:

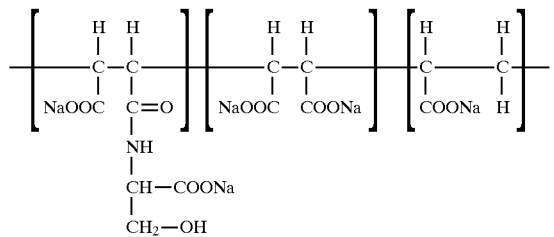

and contained a monomer (a2) structural unit, a sodium maleate structural unit, and a sodium acrylate structural unit in a molar ratio of 21:18:61.

In addition, the average molecular weight of polymer (2) was measured in the same way as of Example 1. Results provided a weight-average molecular weight (Mw) of 11,000. In this way, it could be confirmed that water-soluble polymer (2) could be synthesized.

EXAMPLE 3

First, a sodium salt of a maleic acid-L-glutamic acid monoamide matter (hereinafter referred to as "monomer (a3)") was synthesized as monomer (a) as follows. A mixture of 147 parts of L-glutamic acid, 167 parts of a 48% aqueous sodium hydroxide solution, and 164 parts of ion-exchanged water was placed into a 4-necked flask of 500 ml in capacity equipped with a thermometer, a pH meter, and a stirrer. Next, while the contents of the flask were maintained at 10° C. or lower under stirred conditions, 49 parts of maleic anhydride was added into the flask over a period of 60 minutes by quantitative dropwise addition (the amine (L-glutamic acid) was excessively added to increase the conversion of maleic anhydride), when a 48% aqueous sodium hydroxide solution was appropriately added to maintain the pH of the aqueous reaction solution at 9 or more. After the addition of maleic anhydride had completed, the stirring of the reaction mixture was continued for 30 minutes while the reaction mixture was maintained at 10° C. or lower. After the reaction had completed, the pH of the reaction mixture was adjusted to 9.5 with a 48% aqueous sodium hydroxide solution. As a result, an aqueous colorless transparent solution with a content of 54.0% was obtained. Then, water was removed from this solution to thereby obtain a powdered white solid substance.

This solid substance was identified by IR and 1H-NMR measurement. Results thereof are as follows:

IR (KBr method): 1700 cm$^{-1}$ (s) (CONHR)
$^1$H-NMR (solvent: D$_2$O):
δ 1.6–2.6 ppm (m, 4H, CH$_2$—CH$_2$)
δ 3.7–4.0 ppm (m, 1H, NH—C$\underline{H}$)
δ 5.8–5.9 ppm (d, 1H, CH=)
δ 6.2–6.3 ppm (d, 1H, CH=)

The presence of an amide bond (CONHR) was confirmed from the IR measurement. In addition, from the $^1$H-NMR spectrum analysis, it could be confirmed that the above-mentioned product, obtained in Example 3, was a compound, namely, monomer (a3), shown by the following structural formula:

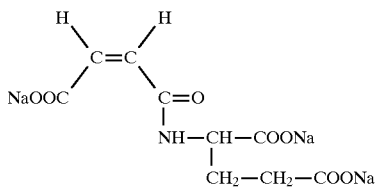

In addition, from an integral ratio of $^1$H-NMR peaks, the conversion of L-glutamic acid was calculated as 41.7%, and that of maleic anhydride as 73.2%. A by-product was formed which was shown by the following structural formula:

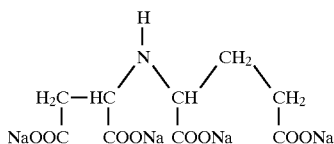

The ratio by weight of their presence was (monomer (a3)):(L-glutamic acid):(maleic acid):(by-product)=48:34:2:16 (any of which was a sodium salt thereof). Thus, the aqueous colorless transparent solution contained monomer (a3).

Using this aqueous colorless transparent solution, a polymer was synthesized as follows. Two hundred parts of this solution (containing 53 parts of monomer (a3) and 2 parts of sodium maleate as monomer (b)) was placed into a 4-necked separable flask of 500 ml in capacity equipped with a thermometer, a stirrer, and a reflux condenser. After the solution was heated to its boiling point while stirred, 6.7 parts of a 35% aqueous hydrogen peroxide solution was continuously dropwise added into the flask over a period of 30 minutes under stirred conditions. Subsequently, 10.5 parts of a 15% aqueous sodium persulfate solution was continuously dropwise added into the flask under stirred conditions over a period of 70 minutes from the completion of the dropwise addition of the aqueous hydrogen peroxide solution. In parallel with this dropwise addition operation, 35.1 parts of a 80% aqueous solution of acrylic acid as monomer (b) was also continuously dropwise added into the aqueous reaction solution over a period of 90 minutes from the initiation of the dropwise addition of the aqueous hydrogen peroxide solution. After the dropwise addition of all materials had completed, the reaction solution was maintained at its boiling point for 60 minutes to carry out a polymerization reaction. In this reaction, the molar ratio of monomer (a3), sodium maleate, and acrylic acid was 30:1:69.

After the reaction had completed, the pH was adjusted to 8.5 with a 48% aqueous sodium hydroxide solution, thereby obtaining an aqueous dark brown transparent solution with a solid content of 48.1%. Next, a post-treatment of removing residual monomers and low molecular weight products from the resultant aqueous solution was carried out in the same way as of Example 1, thereby obtaining an aqueous pale brown transparent solution, with a solid content of 4.5% and pH of 10.0, of a polymer (hereinafter referred to as "polymer (3)"). Then, the water content was removed from this solution to thereby obtain a white powder.

This white powder was measured by IR and $^1$H-NMR. Results thereof are as follows:

IR (KBr method): 1700 cm$^{-1}$ (s) (CONHR)

$^1$H-NMR (solvent: D$_2$O): δ 4–4.4 ppm (m, NH—C$\underline{H}$)

From the above-mentioned results, it was confirmed that an amide bond (CONHR) was present in the resultant polymer, and it was clear that monomer (a3) was introduced into polymer (3). In addition, from analysis of the integral ratio of proton in the $^1$H-NMR spectrum, it could be confirmed that polymer (3) was shown by the following structural formula:

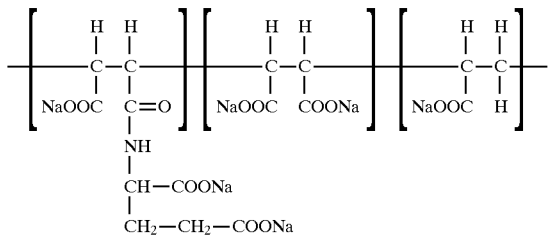

and contained a monomer (a3) structural unit, a sodium maleate structural unit, and a sodium acrylate structural unit in a molar ratio of 31:27:42.

In addition, the average molecular weight of polymer (3) was measured in the same way as of Example 1. Results provided a weight-average molecular weight (Mw) of 4,200. In this way, it could be confirmed that water-soluble polymer (3) could be synthesized.

In the following Example 4 and Referential Examples 1–5, powders of polymers (1) to (3), obtained by the post-treatment of removing residual monomers and by-products in Examples 1 to 3, were used.

Referential Example 1

The calcium ion stabilization degree constant (pKCa) and the calcium ion scavengeability were measured by the below-mentioned method to examine the chelatability of polymers (1) to (3) as obtained in Examples 1 to 3. Results thereof are shown in Table 1.

(Calcium ion stabilization degree constant)

(1) Calcium ion solutions having concentrations of 0.002 mol/L, 0.003 mol/L and 0.004 mol/L respectively were prepared (using CaCl$_2$), and 50 g of each of these solutions was charged into respective beakers of 100 cc in capacity;

(2) 50 mg portions of the powder of polymer (1) were added respectively into the beakers of (1) above;

(3) the pH of each of the solutions in the beakers was adjusted to 10 (using a dilute aqueous sodium hydroxide solution);

(4) 0.15 g of an NaCl powder was added as a stabilizer for a calcium ion electrode; and (5) the concentration of a free calcium ion was measured using the calcium ion electrode. Provided that the concentration of a free calcium ion, the concentration of a calcium ion fixed on the polymer, the number of the free chelate sites, the number of the entire chelate sites, and the stabilization degree constant are denoted by [Ca], [CaS], [S], [S$_0$], and Log K respectively, then equalities [Ca]·[S]/[CaS]=1/K and [S]=[S$_0$]–[CaS] are established. Accordingly, from both equalities, [Ca]·[CaS]=(1/[S$_0$])·[Ca]+1/([S$_0$]·K). Thus, [Ca]/[CaS] and [Ca] were plotted on the vertical and the horizontal axis respectively to calculate [S$_0$], K, and Log K from the slope and the intercept. Log K was taken as a pKCa value.

(6) The operations of (1) to (5) above were also carried out for polymers (2) and (3) in the same way as for polymer (1).

(Calcium ion scavengeability)

(1) A calcium ion solution having a concentration of 0.001 mol/L was prepared (using CaCl$_2$), and 50 g of this solution was charged into a beaker of 100 cc in capacity;

(2) 10 mg of the powder of polymer (1) was added into the beaker of (1) above;

(3) the pH of the resultant aqueous solution in the beaker was adjusted to 9–11 (using a dilute aqueous sodium hydroxide solution);

(4) 1 cc of a 4 mol/L aqueous KCl solution was added as a stabilizer for a calcium ion electrode; and (5) the concentration of a free calcium ion was measured using the calcium ion electrode. A scavenged calcium ion was calculated from the resultant numerical value of the concentration of a free calcium ion to determine by calculation how many milligrams of calcium ion was scavenged in terms of calcium carbonate (CaCO$_3$) per gram of the polymer. The resultant calculated value was taken as the calcium ion scavengeability.

(6) The operations of (1) to (5) above were also carried out for polymers (2) and (3) in the same way as for polymer (1).

Comparative Example 1

The same evaluation as of Referential Example 1 was carried out using sodium polyacrylate with a weight-average molecular weight of 5,000 which was a conventional compound. Results thereof are shown in Table 1.

Comparative Example 2

The same evaluation as of Referential Example 1 was carried out using sodium polymaleate with a weight-average molecular weight of 800 which was a conventional compound. Results thereof are shown in Table 1.

Comparative Example 3

The same evaluation as of Referential Example 1 was carried out using a sodium salt of a maleic acid-acrylic acid copolymer with a molar ratio of a maleic acid structural unit content to an acrylic acid structural unit content of 3:7 and a weight-average molecular weight of 5,000 which was a conventional compound. Results thereof are shown in Table 1.

Comparative Example 4

The same evaluation as of Referential Example 1 was carried out using sodium citrate which was a conventional compound. Results thereof are shown in Table 1.

Comparative Example 5

The same evaluation as of Referential Example 1 was carried out using a mixture of 7:3 in weight ratio of the copolymer, as used in Comparative Example 3, and sodium asparagate which was a conventional compound. Results thereof are shown in Table 1.

TABLE 1

|  | pKCa | Calcium ion scavengeability (mg per g of polymer) |
|---|---|---|
| Referential Example 1 | | |
| Polymer (1) | 4.3 | 290 |
| Polymer (2) | 4.6 | 310 |
| Polymer (3) | 4.0 | 260 |
| Comparative Example 1 | 4.0 | 240 |
| Comparative Example 2 | 3.5 | 280 |
| Comparative Example 3 | 3.4 | 250 |
| Comparative Example 4 | 3.2 | 280 |
| Comparative Example 5 | 2.9 | 200 |

EXAMPLE 4

Detergent compositions containing polymers (1) to (3) above, respectively, in a ratio of 20% (in terms of solid content), which were compositions according to embodiments of the present invention, were prepared using the polymer powders as obtained in Examples 1 to 3. The respective types and amounts of the components of these detergent compositions are shown in Table 2.

TABLE 2

| (Detergent composition) | |
|---|---|
| Components | % by weight |
| Sodium salt of linear chain alkylbenzenesulfonic acid (C = 11.5) | 20 |
| Polyoxyethylene alkyl ether (C = 12, EO = 8) | 15 |
| Zeolite | 20 |
| Enzyme (protease) | 0.5 |
| Polymer | 20 |
| Sodium carbonate | 15 |
| #1 Sodium silicate | 9.5 |

Artificial grime was prepared to evaluate performance of the above-mentioned detergent compositions. The respective types and amounts of the components of this artificial grime are shown in Table 3 below.

TABLE 3

| (Composition of grime) | |
|---|---|
| Components | % by weight |
| Carbon black (designated by JAPAN OIL CHEMIST'S SOCIETY) | 0.5 |
| Clay | 49.75 |
| Myristylic acid | 8.3 |
| Oleic acid | 8.3 |
| Tristearic acid | 8.3 |
| Triolein | 8.3 |
| Cholesterin | 4.38 |
| Cholesterin stearate | 1.09 |
| Paraffin wax (m.p. 50–52° C.) | 0.552 |
| Squalene | 0.552 |

A washing performance test was carried out using the above-mentioned artificial grime as follows. First, the artificial grime was dispersed into carbon tetrachloride to prepare an artificial grime dispersion, and white cotton cloth was then passed through this dispersion, dried, and cut to make 10 cm×10 cm dirty cloth. Next, this dirty cloth was washed under washing conditions as shown in Table 4 below.

TABLE 4

| Washing conditions | |
|---|---|
| Temperature | 20° C. |
| Bath ratio | 1/60 |
| Detergent concentration | 0.3% |
| Water quality | Tap water |
| Terg-O-Tometer | 10 minutes |

(Footnote)
Terg-O-Tometer: made by Ueshima Seisakusho Co., Ltd.

After the washing, the cloth was dried, and then its reflectivity was measured by a predetermined method. The washing ratio was determined from the reflectivity on the basis of the following formula:

Washing ratio={(reflectivity of dirty cloth after washing)−(reflectivity of dirty cloth before washing)}/{(reflectivity of white cloth)−(reflectivity of dirty cloth before washing)}×100.

Results are shown in Table 5.

Comparative Example 6

The same evaluation as of Example 4 was carried out using sodium polyacrylate with a weight-average molecular weight of 5,000 which was a conventional compound. Results thereof are shown in Table 5.

Comparative Example 7

The same evaluation as of Example 4 was carried out using sodium polymaleate with a weight-average molecular weight of 800 which was a conventional compound. Results thereof are shown in Table 5.

Comparative Example 8

The same evaluation as of Example 4 was carried out using a sodium salt of a maleic acid-acrylic acid copolymer with a molar ratio of a maleic acid structural unit content to an acrylic acid structural unit content of 3:7 and a weight-average molecular weight of 5,000 which was a conventional compound. Results thereof are shown in Table 5.

Comparative Example 9

The same evaluation as of Example 4 was carried out using sodium citrate which was a conventional compound. Results thereof are shown in Table 5.

Comparative Example 10

The same evaluation as of Example 4 was carried out using a mixture of 7:3 in weight ratio of the copolymer, as used in Comparative Example 3, and sodium asparagate which was a conventional compound. Results thereof are shown in Table 5.

TABLE 5

| | Washing ratio (%) |
|---|---|
| Example 4 | |
| Polymer (1) | 92 |
| Polymer (2) | 86 |

TABLE 5-continued

| | Washing ratio (%) |
|---|---|
| Polymer (3) | 84 |
| Comparative Example 6 | 82 |
| Comparative Example 7 | 82 |
| Comparative Example 8 | 80 |
| Comparative Example 9 | 80 |
| Comparative Example 10 | 78 |

As is clear from the results of Examples 4 and Comparative Examples 6 to 10 above, the detergent compositions using polymers (1) to (3) according to embodiments of the present invention have higher washing ratios when compared with the cases where conventional compounds are used as detergent compositions.

Referential Example 2

Fiber-treating agents as compositions containing polymers (1) to (3) above in a ratio of 2 g/L (in terms of solid content), which were compositions according to embodiments of the present invention, were prepared using the polymer powders as obtained in Examples 1 to 3. The respective types and amounts of the components of these fiber-treating agents are shown below, which fiber-treating agents are aqueous solutions.

(Components of fiber-treating agents)
Any one of polymers (1) to (3): 2 g/L
Hydrogen peroxide: 10 g/L
Sodium hydroxide: 2 g/L
3 Sodium silicate: 5 g/L Using the above-mentioned fiber-treating agents, a bleaching test was carried out as follows. Plain stitch-knitted, scoured cotton fabric was used as the test cloth. Bleaching conditions are as follows:

(Bleaching conditions)
Hardness of water used: 35.DH (German hardness)
Bath ratio: 1:25
Temperature: 85° C.
Duration: 20 minutes The feeling of the bleached cloth was judged by a sensory examination method. In addition, the degree of whiteness was measured using a 3M color computer SM-3 model, made by SUGA TEST MACHINE Co., to determine the degree of whiteness (W value) from the following whiteness degree formula in a Lab system for evaluation.

$$W=100-[(100-L)^2+a^2+b^2]^{1/2}$$

where:
L is a lightness measured;
a is a red chromaticness index measured; and
b is a blue chromaticness index measured.

The sewability was evaluated by the number of places where base yarn of the cloth was broken in the case where 4 sheets of the cloth were placed upon each other to sew them by 30 cm using a needle #11S with a main sewing machine, but using no sewing yarn. Results thereof are shown in Table 6.

Comparative Example 11

The same evaluation as of Referential Example 2 was carried out using sodium polyacrylate with a weight-average molecular weight of 5,000 which was a conventional compound. Results thereof are shown in Table 6.

Comparative Example 12

The same evaluation as of Referential Example 2 was carried out using sodium polymaleate with a weight-average molecular weight of 800 which was a conventional compound. Results thereof are shown in Table 6.

Comparative Example 13

The same evaluation as of Referential Example 2 was carried out using a sodium salt of a maleic acid-acrylic acid copolymer with a molar ratio of a maleic acid structural unit content to an acrylic acid structural unit content of 3:7 and a weight-average molecular weight of 5,000 which was a conventional compound. Results thereof are shown in Table 6.

Comparative Example 14

The same evaluation as of Referential Example 2 was carried out using sodium citrate which was a conventional compound. Results thereof are shown in Table 6.

Comparative Example 15

The same evaluation as of Referential Example 2 was carried out using a mixture of 7:3 in weight ratio of the copolymer, as used in Comparative Example 3, and sodium asparagate which was a conventional compound. Results thereof are shown in Table 6.

TABLE 6

(Evaluation as fiber-treating agents)

| | Feeling *1) | Degree of whiteness (W value) | Sewability (number of base yarn-broken places) |
|---|---|---|---|
| Referential Example 2 | | | |
| Polymer (1) | ○ | 93 | 45 |
| Polymer (2) | ○ | 92 | 41 |
| Polymer (3) | ○ | 88 | 55 |
| Comparative Example 11 | Δ | 86 | 70 |
| Comparative Example 12 | Δ | 88 | 69 |
| Comparative Example 13 | X | 86 | 58 |
| Comparative Example 14 | X | 86 | 79 |
| Comparative Example 15 | X | 82 | 79 |

*1) Feeling:
soft ○
somewhat hard Δ
considerably hard X

As is clear from the results of Referential Examples 2 and Comparative Examples 11 to 15 above, the fiber-treating agents using polymers (1) to (3) according to embodiments of the present invention are excellent with regard to the feeling and the whiteness degree, and greatly decreased in the number of the base yarn-broken places, when compared with the cases where conventional compounds are used as fiber-treating agents.

Referential Example 3

Using polymers (1) to (3) above as water-treating agents, a heating treatment was made under the below-mentioned conditions to carry out a calcium carbonate scale inhibitability test.

Calcium chloride of 780 ppm and sodium hydrogen carbonate of 1,500 ppm, followed by each of the powders of polymers (1) to (3) as obtained in Examples 1 to 3, were added into ion-exchanged water, thereby preparing an aqueous solution with a concentration of calcium carbonate of 530 ppm and a concentration of each of the polymers of 3 ppm. This solution was heated at 70° C. for 8 hours. The heated solution was cooled and then filtrated with a 0.1 μm membrane filter. The resultant filtrate was analyzed in accordance with JIS K0101 to evaluate a calcium carbonate scale inhibitability on the basis of the following formula:

Scale inhibitability=[(C-B)/(A-B)]×100 where:
- A is a concentration of calcium which was dissolved in the solution before the test;
- B is a concentration of calcium in a filtrate to which no water-treating agent is added; and
- C is a concentration of calcium in a filtrate after the test.

Results thereof are shown in Table 7.

Comparative Example 16

The same evaluation as of Referential Example 3 was carried out using sodium polyacrylate with a weight-average molecular weight of 5,000 which was a conventional compound. Results thereof are shown in Table 7.

Comparative Example 17

The same evaluation as of Referential Example 3 was carried out using sodium polymaleate with a weight-average molecular weight of 800 which was a conventional compound. Results thereof are shown in Table 7.

Comparative Example 18

The same evaluation as of Referential Example 3 was carried out using a sodium salt of a maleic acid-acrylic acid copolymer with a molar ratio of a maleic acid structural unit content to an acrylic acid structural unit content of 3:7 and a weight-average molecular weight of 5,000 which was a conventional compound. Results thereof are shown in Table 7.

Comparative Example 19

The same evaluation as of Referential Example 3 was carried out using sodium citrate which was a conventional compound. Results thereof are shown in Table 7.

Comparative Example 20

The same evaluation as of Referential Example 3 was carried out using a mixture of 7:3 in weight ratio of the copolymer, as used in Comparative Example 3, and sodium asparagate which was a conventional compound. Results thereof are shown in Table 7.

TABLE 7

(Evaluation as water-treating agents)

| | Scale inhibitability (%) |
|---|---|
| Referential Example 3 | |
| Polymer (1) | 73 |
| Polymer (2) | 70 |
| Polymer (3) | 68 |
| Comparative Example 16 | 63 |
| Comparative Example 17 | 53 |
| Comparative Example 18 | 65 |
| Comparative Example 19 | 45 |
| Comparative Example 20 | 55 |

As is clear from the results of Referential Examples 3 and Comparative Examples 16 to 20 above, the water-treating agents using polymers (1) to (3) according to embodiments of the present invention are excellent with regard to the scale inhibitability when compared with the cases where conventional compounds are used as water-treating agents.

Referential Example 4

Using polymers (1) to (3) above as inorganic-pigment dispersants, inorganic-pigment dispersions were prepared as follows:

Four hundred parts of a cake (solid content: 65.3%), as dehydrated by filter press, of calcite type cubic light calcium carbonate (primary particle diameter: 0.15 μm) was placed into a beaker (material quality: SUS 304, inner diameter: 90 mm, height: 160 mm) having a capacity of 1 liter. Next, 1.3 parts of the polymer as the inorganic-pigment dispersant (the ratio of the polymer to the weight of the calcium carbonate was 0.5% in terms of solid content) and 8.9 parts of water for adjusting the solid content were added into the beaker, and the materials in the beaker were mixed by kneading at a low speed for 3 minutes using a dissolver stirring wing (50 mm ø). Then, a dispersing operation was carried out at 3,000 rpm for 10 minutes to thereby obtain a dispersion having a solid content of 64%.

The viscosity of the resultant water dispersion was measured with a B type viscometer at 25° C. twice, namely, just after the above-mentioned dispersing operation and after standing stationary at room temperature for 1 week. Results of the measurement are shown in Table 8.

Comparative Example 21

The same evaluation as of Referential Example 4 was carried out using sodium polyacrylate with a weight-average molecular weight of 5,000 which was a conventional compound. Results thereof are shown in Table 8.

Comparative Example 22

The same evaluation as of Referential Example 4 was carried out using sodium polymaleate with a weight-average molecular weight of 800 which was a conventional compound. Results thereof are shown in Table 8.

Comparative Example 23

The same evaluation as of Referential Example 4 was carried out using a sodium salt of a maleic acid-acrylic acid copolymer with a molar ratio of a maleic acid structural unit content to an acrylic acid structural unit content of 3:7 and a weight-average molecular weight of 5,000 which was a conventional compound. Results thereof are shown in Table 8.

Comparative Example 24

The same evaluation as of Referential Example 4 was carried out using sodium citrate which was a conventional compound. Results thereof are shown in Table 8.

Comparative Example 25

The same evaluation as of Referential Example 4 was carried out using a mixture of 7:3 in weight ratio of the copolymer, as used in Comparative Example 3, and sodium asparagate which was a conventional compound. Results thereof are shown in Table 8.

TABLE 8

(Evaluation as inorganic-pigment dispersants)

| | Viscosity of dispersion (cps) | |
|---|---|---|
| | Just after dispersing | After standing stationary for 1 week |
| Referential Example 4 | | |
| Polymer (1) | 350 | 410 |
| Polymer (2) | 360 | 430 |
| Polymer (3) | 400 | 460 |
| Comparative Example 21 | 450 | 600 |
| Comparative Example 22 | 3,000 | unmeasurable |
| Comparative Example 23 | 700 | 800 |
| Comparative Example 24 | 10,000 | unmeasurable |
| Comparative Example 25 | 1,000 | 1,300 |

As is clear from the results of Referential Examples 4 and Comparative Examples 21 to 25 above, the dispersions using polymers (1) to (3) according to embodiments of the present invention have high dispersing strength and, even after standing stationary for 1 week, maintain good dispersibility, when compared with dispersions using conventional compounds.

Referential Example 5

Using polymers (1) to (3) above as wood pulp-bleaching assistants (pretreatment agents), wood pulp was bleached as follows:

First, 30 parts in terms of absolute dry weight of ground pulp was placed into a beaker of 5 liters in capacity, and then 3,000 parts of water of 50° C. in temperature and 0.06 parts of the polymer as the bleaching assistant (the ratio of the polymer to the weight of the pulp was 0.2%) were added into the beaker. The contents of the beaker were stirred at 50° C. for 15 minutes. Next, the pulp was separated from the treating solution by filtration with No. 2 filter paper, and then washed by passing 1,500 parts of water through the pulp, and then dehydrated.

Next, the above-pretreated pulp was placed into a beaker of 5 liters in capacity, and then water was added into the beaker to finally have a pulp concentration of 14%. Furthermore, hydrogen peroxide (of which the ratio to the weight of the pulp was 4%), #3 sodium silicate, and sodium hydroxide were added into the beaker to thereby adjust the pH of the resultant treating solution to 11.0.

This treating solution was transferred into a polyethylene-made bag, of which the opening portion was then folded to prevent the water content from vaporing. This bag was heated for 5 hours in a water bath as had beforehand been adjusted to 65° C., whereby the pulp was bleached. Then, the bleached pulp was filtrated with 420-mesh filter cloth and then dehydrated. The concentration of hydrogen peroxide remaining in the resultant filtrate was measured to determine a hydrogen peroxide consumption ratio by calculation on the basis of the following formula:

$$\text{Hydrogen peroxide consumption ratio} = [(B-C)/B] \times 100$$

where:

B is a concentration (%) of hydrogen peroxide in the treating solution before the bleaching; and C is a concentration (%) of hydrogen peroxide in the treating solution after the bleaching.

In addition, a portion of the bleached pulp was diluted to 3% with water and then adjusted to 4.5 in pH with an aqueous sulfurous acid solution, thereby obtaining a pulp slurry. Using this pulp slurry, two handmade sheets was prepared by a TAPPI (Technical Association of the Pulp and Paper Industry) standard method. These sheets were naturally dried, and then their whiteness degrees were measured with a Hunter's whiteness degree meter. Results of the measurement are shown in Table 9.

Comparative Example 26

The same evaluation as of Referential Example 5 was carried out using sodium polyacrylate with a weight-average molecular weight of 5,000 which was a conventional compound. Results thereof are shown in Table 9.

Comparative Example 27

The same evaluation as of Referential Example 5 was carried out using sodium polymaleate with a weight-average molecular weight of 800 which was a conventional compound. Results thereof are shown in Table 9.

Comparative Example 28

The same evaluation as of Referential Example 5 was carried out using a sodium salt of a maleic acid-acrylic acid copolymer with a molar ratio of a maleic acid structural unit content to an acrylic acid structural unit content of 3:7 and a weight-average molecular weight of 5,000 which was a conventional compound. Results thereof are shown in Table 9.

Comparative Example 29

The same evaluation as of Referential Example 5 was carried out using sodium citrate which was a conventional compound. Results thereof are shown in Table 9.

Comparative Example 30

The same evaluation as of Referential Example 5 was carried out using a mixture of 7:3 in weight ratio of the copolymer, as used in Comparative Example 3, and sodium asparagate which was a conventional compound. Results thereof are shown in Table 9.

TABLE 9

(Evaluation of performance as wood pulp-bleaching assistants)

| | Hydrogen peroxide consumption ratio (%) | Hunter's whiteness degree (%) |
|---|---|---|
| Referential Example 5 | | |
| Polymer (1) | 71.0 | 81.6 |
| Polymer (2) | 70.5 | 78.3 |
| Polymer (3) | 69.8 | 74.6 |
| Comparative Example 26 | 77.3 | 75.9 |
| Comparative Example 27 | 79.8 | 75.3 |
| Comparative Example 28 | 81.0 | 74.2 |
| Comparative Example 29 | 84.9 | 70.5 |

TABLE 9-continued (Evaluation of performance as wood pulp-bleaching assistants)

|  | Hydrogen peroxide consumption ratio (%) | Hunter's whiteness degree (%) |
|---|---|---|
| Comparative Example 30 | 87.2 | 71.0 |

As is clear from the results of Referential Examples 5 and Comparative Examples 26 to 30 above, the bleaching assistants using polymers (1) to (3) according to embodiments of the present invention display excellent whiteness degrees and low hydrogen peroxide consumption ratios, and therefore can decrease the amount of hydrogen peroxide being used and are economical, when compared with bleaching-assistants using conventional compounds.

EXAMPLE 5

A mixture of 33.2 parts of DL-asparagic acid, 41.7 parts of a 48% aqueous sodium hydroxide solution, and 13.6 parts of ion-exchanged water was placed into a 4-necked flask of 100 ml in capacity equipped with a thermometer, a pH meter, and a stirrer. Next, while the contents of the flask were maintained at 10° C. or lower under stirred conditions, 24.5 parts of maleic anhydride was added into the flask over a period of 60 minutes by quantitative dropwise addition, when a 48% aqueous sodium hydroxide solution was appropriately added to maintain the pH of the aqueous reaction solution at 9 or more. After the addition of maleic anhydride had completed, the stirring of the reaction mixture was continued for 30 minutes while the reaction mixture was maintained at 10° C. or lower. After the reaction had completed, 14.7 parts of ion-exchanged water was added, and the pH of the reaction mixture was then adjusted to 11.5 with a 48% aqueous sodium hydroxide solution. As a result, an aqueous brown transparent solution was obtained. Then, water was removed from this solution to thereby obtain a powdered white solid substance.

This solid substance was identified by IR and $^1$H-NMR measurement. Results thereof are as follows:

IR (KBr method): 1700 cm$^{-1}$ (s) (CONHR)

$^1$H-NMR (solvent: D$_2$O):

δ 2.2–2.6 ppm (m, 2H, CH$_2$)

δ 4.2–4.4 ppm (m, 1H, NH—C$\underline{H}$)

δ 5.7–5.8 ppm (d, 1H, CH=)

δ 6.2–6.3 ppm (d, 1H, CH=)

The presence of an amide bond (CONHR) was confirmed from the IR measurement. In addition, from the $^1$H-NMR spectrum analysis, it could be confirmed that the above-mentioned product, obtained in Example 5, was a compound shown by the following structural formula:

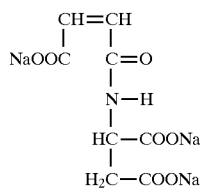

EXAMPLE 6

A mixture of 10.5 parts of DL-serine, 8.3 parts of a 48% aqueous sodium hydroxide solution, and 6.6 parts of ion-exchanged water was placed into a 4-necked flask of 100 ml in capacity equipped with a thermometer, a pH meter, and a stirrer. Next, while the contents of the flask were maintained at 10° C. or lower under stirred conditions, 19.6 parts of maleic anhydride was added into the flask over a period of 60 minutes by quantitative dropwise addition, when a 48% aqueous sodium hydroxide solution was appropriately added to maintain the pH of the aqueous reaction solution at 9 or more. After the addition of maleic anhydride had completed, the stirring of the reaction mixture was continued for 30 minutes while the reaction mixture was maintained at 10° C. or lower. After the reaction had completed, 11.4 parts of ion-exchanged water was added, and the pH of the reaction mixture was then adjusted to 12.5 with a 48% aqueous sodium hydroxide solution. As a result, an aqueous colorless transparent solution was obtained. Then, water was removed from this solution to thereby obtain a powdered white solid substance.

This solid substance was identified by IR and $^1$H-NMR measurement. Results thereof are as follows:

IR (KBr method): 1700 cm$^{-1}$ (s) (CONHR)

$^1$H-NMR (solvent: D$_2$O):

δ 3.6–3.8 ppm (m, 2H, C$\underline{H_2}$—OH)

δ 4.0 ppm (m, 1H, NH—C$\underline{H}$)

δ 5.8–5.9 ppm (d, 1H, CH=)

δ 6.2–6.3 ppm (d, 1H, CH=)

The presence of an amide bond (CONHR) was confirmed from the IR measurement. In addition, from the $^1$H-NMR spectrum analysis, it could be confirmed that the above-mentioned product, obtained in Example 6, was a compound shown by the following structural formula:

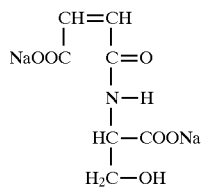

EXAMPLE 7

A mixture of 14.7 parts of L-glutamic acid, 16.7 parts of a 48% aqueous sodium hydroxide solution, and 16.4 parts of ion-exchanged water was placed into a 4-necked flask of 100 ml in capacity equipped with a thermometer, a pH meter, and a stirrer. Next, while the contents of the flask were maintained at 10° C. or lower under stirred conditions, 0.5 parts of maleic anhydride was added into the flask over a period of 60 minutes by quantitative dropwise addition, when a 48% aqueous sodium hydroxide solution was appropriately added to maintain the pH of the aqueous reaction solution at 9 or more. After the addition of maleic anhydride had completed, the stirring of the reaction mixture was continued for 30 minutes while the reaction mixture was maintained at 10° C. or lower. After the reaction had completed, the pH of the reaction mixture was adjusted to 9.5 with a 48% aqueous sodium hydroxide solution. As a result, an aqueous colorless transparent solution was obtained. Then, water was removed from this solution to thereby obtain a powdered white solid substance.

This solid substance was identified by IR and $^1$H-NMR measurement. Results thereof are as follows:

IR (KBr method): 1700 cm$^{-1}$ (s) (CONHR)

$^1$H-NMR (solvent: D$_2$O):

δ 1.6–2.6 ppm (m, 4H, CH$_2$—CH$_2$)

δ 3.7–4.0 ppm (m, 1H, NH—C$\underline{H}$)

δ 5.8–5.9 ppm (d, 1H, CH=)

δ 6.2–6.3 ppm (d, 1H, CH=)

The presence of an amide bond (CONHR) was confirmed from the IR measurement. In addition, from the $^1$H-NMR spectrum analysis, it could be confirmed that the above-mentioned product, obtained in Example 7, was a compound shown by the following structural formula:

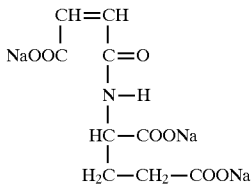

EXAMPLE 8

A mixture of 13.3 parts of DL-asparagic acid, 11.7 parts of a 29% aqueous ammonia solution, and 4.9 parts of ion-exchanged water was placed into a 4-necked flask of 100 ml in capacity equipped with a thermometer, a pH meter, and a stirrer. Next, while the contents of the flask were maintained at 10 OC or lower under stirred conditions, 9.8 parts of maleic anhydride was added into the flask over a period of 60 minutes by quantitative dropwise addition, when a 29% aqueous ammonia solution was appropriately added to maintain the pH of the aqueous reaction solution at 9 or more. After the addition of maleic anhydride had completed, the stirring of the reaction mixture was continued for 30 minutes while the reaction mixture was maintained at 10° C. or lower. After the reaction had completed, the pH of the reaction mixture was adjusted to 10.5 with a 29% aqueous ammonia solution. As a result, an aqueous brown transparent solution was obtained. Then, water was removed from this solution to thereby obtain a powdered white solid substance.

This solid substance was identified by IR and $^1$H-NMR measurement. Results thereof are as follows:

IR (KBr method): 1700 cm$^{-1}$ (s) (CONHR)

$^1$H-NMR (solvent: D$_2$O):

δ 2.2–2.9 ppm (m, 2H, CH$_2$)

δ 4.2–4.3 ppm (m, 1H, NH—C$\underline{H}$)

δ 5.7–5.8 ppm (d, 1H, CH=)

δ 6.2–6.3 ppm (d, 1H, CH=)

The presence of an amide bond (CONHR) was confirmed from the IR measurement. In addition, from the $^1$H-NMR spectrum analysis, it could be confirmed that the above-mentioned product, obtained in Example 8, was a compound shown by the following structural formula:

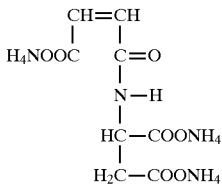

It is clear from the above-mentioned structural formulae that the compounds, as obtained in Examples 5 to 8, can form polymers, which have monomer units derived from monomers shown by the respective structural formulae, by radical polymerization. Because these polymers have the above-mentioned monomer units, they have water solubility and high scavengeability to heavy metals and can scavenge a large amount of metal ions per unit weight of the polymers.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A water-soluble polymer having a weight-average molecular weight of about 1,000 to about 20,000 and a structural unit having the following general formula (2):

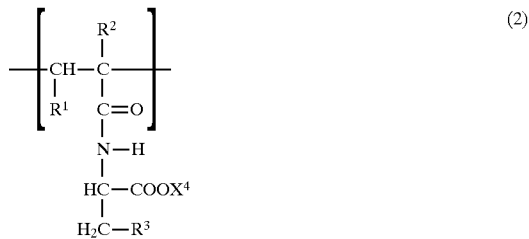

wherein
$R^1$ is H or COOX$^1$;
$R^2$ is H or CH$_2$COOX$^2$;
$R^3$ is COOX$^3$, OH or CH$_2$COOX$^3$;
$X^1$ is H, Na, K or NH$_4$;
$X^2$ is H, Na, K or NH$_4$;
$X^3$ is H, Na, K or NH$_4$;
$X^4$ is H, Na, K or NH$_4$;
and wherein $R^1$ and $R^2$ are not both H.

2. The water-soluble polymer according to claim 1 wherein the structural unit is in the polymer in the range of about 1 to about 100 mol %.

3. The water-soluble polymer according to claim 1 prepared by a process comprising the step of polymerizing in an aqueous medium a monomer including a compound having the following general formula (1):

wherein
$R^1$ is H or COOX$^1$;
$R^2$ is H or CH$_2$COOX$^2$;
$R^3$ is COOX$^3$, OH or CH$_2$COOX$^3$;
$X^1$ is H, Na, K or NH$_4$;
$X^2$ is H, Na, K or NH$_4$;
$X^3$ is H, Na, K or NH$_4$;
$X^4$ is H, Na, K or NH$_4$;
and wherein $R^1$ and $R^2$ are not both H.

4. The water-soluble polymer according to claim 2 wherein the structural unit is in the polymer in the range of about 10 to about 40 mol %.

5. The water-soluble polymer according to claim 1 wherein $R^1$, $R^2$ and $R^3$ in the general formula (2) are $R^1$=COOX$^1$, $R^2$=H and $R^3$=COOX$^3$.

6. The water-soluble polymer according to claim 1 wherein $R^1$, $R^2$ and $R^3$ in the general formula (2) are $R^1$=COOX$^1$, $R^2$=H and $R^3$=OH.

7. The water-soluble polymer according to claim 1 wherein $R^1$, $R^2$ and $R^3$ in the general formula (2) are $R^1=COOX^1$, $R^2=H$ and $R^3=CH_2COOX^3$.

* * * * *